(12) United States Patent
Bresin et al.

(10) Patent No.: US 8,895,532 B2
(45) Date of Patent: Nov. 25, 2014

(54) USE OF HYALURONIC ACID FOR THE PREPARATION OF COMPOSITIONS INTENDED FOR IMPROVING IN PARTICULAR THE PROTECTIVE FUNCTION OF THE SKIN, THE EYE AND THE MUCOUS MEMBRANES

(75) Inventors: Anthony Bresin, Saint Masmes (FR); Edith Puchelle, Tauriac (FR); Jean-Marie Zahm, Reims (FR); Magali Milliot, Reims (FR)

(73) Assignees: Agro Industrie Recherches et Developpements A.R.D., Pomacle (FR); INSERM (Institut National de la Sante et de la Recherche Medicale), Paris (FR)

( * ) Notice: Subject to any disclaimer, the term of this patent is extended or adjusted under 35 U.S.C. 154(b) by 588 days.

(21) Appl. No.: 12/670,219

(22) PCT Filed: Jul. 4, 2008

(86) PCT No.: PCT/FR2008/000959
§ 371 (c)(1),
(2), (4) Date: May 7, 2010

(87) PCT Pub. No.: WO2009/024677
PCT Pub. Date: Feb. 26, 2009

(65) Prior Publication Data
US 2010/0210585 A1 Aug. 19, 2010

(30) Foreign Application Priority Data
Jul. 23, 2007 (FR) ...................................... 07 05349

(51) Int. Cl.
| | | |
|---|---|---|
| *A61K 31/728* | (2006.01) | |
| *A61K 8/73* | (2006.01) | |
| *A61P 17/00* | (2006.01) | |
| *A61P 1/00* | (2006.01) | |
| *A61Q 19/08* | (2006.01) | |
| *A61P 27/02* | (2006.01) | |
| *A61K 8/67* | (2006.01) | |
| *A61K 9/00* | (2006.01) | |
| *A61K 31/355* | (2006.01) | |
| *A61K 31/375* | (2006.01) | |
| *A61K 45/06* | (2006.01) | |

(52) U.S. Cl.
CPC .............. *A61K 8/671* (2013.01); *A61K 9/0048* (2013.01); *A61K 8/676* (2013.01); *A61K 8/678* (2013.01); *A61K 8/735* (2013.01); *A61K 31/355* (2013.01); *A61K 31/375* (2013.01); *A61K 31/728* (2013.01); *A61K 45/06* (2013.01); *A61Q 19/08* (2013.01)
USPC ......................................................... 514/54

(58) Field of Classification Search
None
See application file for complete search history.

(56) References Cited

U.S. PATENT DOCUMENTS

| | | | | | |
|---|---|---|---|---|---|
| 4,303,676 | A | * | 12/1981 | Balazs ........................... | 514/773 |
| 4,517,295 | A | * | 5/1985 | Bracke et al. .................. | 435/101 |
| 5,166,331 | A | | 11/1992 | Della Valle et al. | |
| 7,241,456 | B2 | * | 7/2007 | Vromen ........................ | 424/449 |

FOREIGN PATENT DOCUMENTS

| | | | |
|---|---|---|---|
| FR | 2 847 818 | A | 6/2004 |
| JP | 59-219209 | * | 10/1984 |
| WO | 00/01394 | A | 1/2000 |
| WO | 02/069984 | A | 9/2002 |
| WO | 2006/072243 | A | 7/2006 |

OTHER PUBLICATIONS

Fujawa, P. et al "Effect of molecular weight on the exponential growth . . . " JACS (2005) vol. 127, pp. 9224-9234.*
Guttman, J. et al "Tight junctions as targets of infectious agents" BBA (2009) vol. 1788, pp. 832-841.*
Turner, J. "Molecular basis of epithelial barrier regulation" Am. J. Pathol. (2006) vol. 169, No. 6, pp. 1901-1909.*
Dagli, U. et al "The role of reactive oxygen metabolites . . . " Inflam. Bowel Dis. (1997) vol. 3, No. 4, pp. 260-264.*
English translation of JP 59-219209 (1984).*
Nakamura M et al, "Recent developments in the use of hyaluronan in wound healing", Expert Opinion on Investigational Drugs, vol . 4, No. 3, Jan. 1, 1995 , pp. 175-188, Ashley Publications Ltd., London, GB.
"Martindale", 1999, pp. 1365-1370, Pharmaceutical Press , London, UK.
Morganti P et al, "B iweekly i n-offce injectable treatment of striae distensae vs a long-term daily use of topical vitamin C", Journal of Applied Cosmetology 200110 IT, vol. 19, No. 4, Oct. 2001, pp. 107-112.
Di Pietro a et al, "Role of hyaluronic acid and vitamin C in photoageing", Journal of Applied Cosmetology 1998 IT, vol. 16, No. 4, 1998, pp. 125-133.
International Search Report in Corresponding International Application PCT/FR2008/000959 Dated Oct. 21, 2009.
French Search Report in Corresponding Applications FA 699215, FR 0705349 Dated Mar. 4, 2008.

* cited by examiner

*Primary Examiner* — Leigh Maier
(74) *Attorney, Agent, or Firm* — Young & Thompson

(57) ABSTRACT

The present invention relates to the use of hyaluronic acid for the preparation of compositions intended for improving the protective function of the skin, the eye and the mucous membranes, in particular of the upper and lower airways and the intestinal mucosa.

18 Claims, 8 Drawing Sheets

USE OF HYALURONIC ACID FOR THE PREPARATION OF COMPOSITIONS INTENDED FOR IMPROVING IN PARTICULAR THE PROTECTIVE FUNCTION OF THE SKIN, THE EYE AND THE MUCOUS MEMBRANES

The present invention relates to the use of hyaluronic acid for the preparation of compositions intended for improving the protective function of the skin, the eye and the mucous membranes, in particular of the upper and lower airways and the intestinal mucosa.

The mucous membranes of the airways and the intestinal mucosa, the skin and the eye are lined with a surface epithelium forming a continuous lining and constituting a physical protection barrier the effectiveness of which is dependant on an equilibrium between the stressors and the numerous defence mechanisms available to this epithelium.

Among these mechanisms, the surface epithelium plays a key role in defence mechanisms such as the inflammatory reaction, the immune response, the transepithelial transport of electrolytes and the secretion of molecules with an anti-infectious activity. The majority of these functions require the maintenance of a cellular interaction and a polarity. Any alteration to the epithelium can lead to the malfunction of these defence mechanisms.

Thus, during acute or chronic bronchial inflammatory phenomena, an alteration of the efficiency of the mucociliary transport, in relation to the inhalation of numerous infectious agents (bacteria, viruses, etc.) or non-infectious agents (particles, atmospheric or workplace pollution), can induce an alteration in the integrity of the epithelial barrier and lead to more or less significant lesions of the respiratory epithelium. These lesions can vary from the loss of the junctionality of the epithelial barrier to complete epithelial desquamation.

The re-epithelialization of the surface of the respiratory epithelium after a lesion is in the first place dependent on the spread and the migration of the cells around the damaged area (Zahm et al., Am J Respir Cell Mol Biol 1991, 5:242-248; Hérard et al., Am J Respir Cell Mol Biol 1996, 15: 624-632). This re-epithelialization must be accompanied by a restoration of the defence function of the epithelial barrier.

The junction complexes of the epithelial cells also play a prominent role in maintaining epithelial integrity.

The function of the epithelial barrier is ensured by three main types of junction complexes:
1) the tight junctions and the intermediate junctions which form intercellular anchoring belts,
2) the desmosomes which are situated at the interface between the basal cells and the cylindrical surface cells and
3) the communicating junctions which are the transduction pathways of intracellular signals.

The tight junctions form a selective barrier regulating the passage of ions and molecules through paracellular space. Under electron microscopy, it is noted that the tight junctions form a series of fusion points between the outer leaflets of the plasma membranes of two adjacent cells. These membrane contact zones appear, by freeze fracture, in the form of a continuous network that surrounds the apex of each cell. This network is constituted by membrane protein polymers, the claudins and occludin which are themselves connected to cytoplasmic proteins among which in particular the zonula occludens proteins (ZO-1 to 3) are to be found. Occludin, the claudins as well as the ZO-1's are often the target for bacterial toxins, leading to an alteration in the organisation and the function of the tight junctions (Coraux et al., Am J Respir Cell Mol Biol 2004, 5:605-612).

Among the junction complexes, the communicating junctions are involved in the transmission of molecules from one cell to the other. They are constituted by a hierarchized assembly of connexins which are grouped together in a hexameric unit, the connexon. Each connexon is associated with the connexon of a neighbouring cell in order to form a 2 to 4 nm tunnel allowing the passage of small-sized molecules.

In addition to these junction complexes ensuring the protection of the epithelium, and in order to prevent colonization and infection by inhaled micro-organisms, the epithelium maintains, thanks to the production of peptides and molecules with bactericide activity, a sterile environment. Among these anti-bacterial agents secreted by the respiratory epithelial cells, it has been shown that the leucoproteinase inhibitor (SLPI) is capable of inducing the death of gram-negative and gram-positive bacteria.

Although the alteration in the defence functions of the tight junctions is initially the consequence of the infectious process, it is also assumed that the significant inflammation which accompanies the infection can be at the origin of modifications in permeability of the epithelial barrier.

The cytokines represent a family of soluble polypeptide molecules of low molecular mass released by a very large number of activated cells during immune and inflammatory processes. Among these cytokines, interleukin 8 (IT-8) is increased in inflammatory and infectious diseases. The chemo-attractant power of IL-8 vis-ż-vis the neutrophils constitute a defence mechanism adapted to the majority of pathological situations, but an exaggerated response by neutrophils can exacerbate the alteration in the defence functions of the respiratory epithelium (Tirouvanziam et al., Am J Respir Cell Mol Biol, 2000, 2:121-127).

The restoration of these defence functions after an attack on the epithelium is therefore an important stage in maintaining the barrier functions of the epithelium and the isolation of molecules capable of promoting this restoration therefore represents a significant challenge.

Currently the treatment of attacks on the epithelium consists above all in a symptomatic treatment: bronchodilators, anti-inflammatories, antibiotics, muco-regulators.

The French patent FR2 847 818 describes a hyaluronic acid, its preparation method and its application in a composition having a therapeutic activity vis-à-vis in particular respiratory affections of the upper airways.

The hyaluronic acid described in this patent has a molecular weight of at most $10^5$ Da. The hyaluronic acid is in particular used in the context of the treatment of respiratory affections of the upper airways (repair of the respiratory epithelium).

The U.S. Pat. No. 6,806,259 describes a preparation of hyaluronic acid with a molecular weight from 50,000 to 200,000 Daltons. This preparation is administered by oral route as a nutritional supplement for softening human skin.

The Application US 2006/166930 relates to a pharmaceutical composition containing acetylated hyaluronic acid for the treatment of dryness of the eye. The molecular weight of the acetylated hyaluronic acid is preferentially from 10,000 to 1,000,000 Daltons.

The U.S. Pat. No. 5,166,331 describes two hyaluronic acid fractions, one with a molecular weight from 50,000 to 100,000 (hyalastine) used for wound healing and the other with a molecular weight from 500,000 to 730,000 (hyalectin) used for intraocular and intraarticular injections.

The Application DE 10 360 425 relates to the use of hyaluronic acid with a molecular weight from 50,000 to 10,000,000 Daltons, a hyaluronic acid salt and/or derivatives thereof for the production of a pharmaceutical composition for the treatment of ophthalmic and/or rhinic complications.

None of these documents, using hyaluronic acid, describes the restoration of the defence functions of the junction complexes after an attack on the epithelium and to date, only cytokines such as for example TGF-beta or the glucocorticoides have been described as being capable of increasing the expression of the intercellular adhesion molecules.

One of the purposes of the invention is the use of hyaluronic acid with a low molecular weight, from 30,000 to 45,000 Daltons in order to stimulate the mechanisms involved in the restoration of the defence functions and having an activity which protects and/or improves the protective functions of the respiratory mucous membranes, the intestinal mucosa, the skin, or the eye, in the case of attacks originating from physical, chemical or microbiological agents.

Another purpose of the invention is to provide pharmaceutical compositions containing hyaluronic acid for the preparation of a medicament intended for the prevention of pathologies such as asthma, respiratory allergies, respiratory distress syndrome.

Another purpose of the invention is to provide cosmetic compositions containing hyaluronic acid intended for improving the protective function of the skin in the context of functional and structural disorders of the skin, or the protective function of the eye in the context of ocular disorders.

Another purpose of the invention is to provide food compositions containing hyaluronic acid intended for improving the protective function of the intestinal mucosa in the context of digestive disorders.

As a result, the present invention relates to the use of at least one hyaluronic acid with a molecular weight from 30,000 to 45,000 Daltons, preferentially 40,000 Daltons, or corresponding salts thereof, for the preparation of compositions intended for the protection and/or the restoration of the integrity of the mucous membranes of the upper and lower airways, the intestinal mucosa, the skin, or the eye, in the case of attacks originating from physical, chemical or microbiological agents, and in which the epithelial cells are involved, in particular the junction complexes of the latter.

Below 30,000 Daltons, the hyaluronic acid becomes inflammatory (U.S. Pat. No. 5,166,331) and above 45,000, the hyaluronic acid loses its activity.

The expression "corresponding salts" designates the salts of sodium, potassium, lithium, calcium, barium, strontium, magnesium, aluminium, ammonium or substituted ammonium.

The expression "respiratory mucous membranes" designates the epithelium of the upper and lower airways, which is pseudostratified, and constituted by hair cells, mucous cells, basal cells, brush cells and neuro-endocrine cells, as well the chorion which is very vascularized and comprises numerous elastic fibres.

The expression "upper airways" comprises the nasal cavity, the pharynx and the larynx and the expression "lower airways" comprises the trachea, the bronchial tubes and the bronchioles.

The expression "intestinal mucosa" designates the inner part of the digestive tract and comprises:

the epithelium which is formed, starting from the stomach, by a single layer of cells connected to one another by occlusive junctions at the level of the edge of their apical surface; exocrine cells which secrete mucus into the lumen as well as endocrine cells which release hormones into the blood, are included in the epithelial layer, the lamina propria, a loose layer of connective tissue very rich in blood and lymphatic capillaries, in leucocytes and other cells of the defence system against microorganisms which are capable of passing through the epithelium, the muscularis mucosae, a thin layer of smooth muscle cells which by contracting can modify the folds of the epithelium.

The expression "physical agents" generally designates sources of energy which are capable of causing lesions or diseases. These are in particular noise, vibrations, radiation (ionizing, such as X and gamma rays or optical such as ultraviolet rays, laser rays and infrared lamps), waves (for example, microwaves or radiofrequency waves) and extreme temperatures and pressures.

The expression "chemical agents" designates the chemical products (non-dangerous, dangerous, non-CMR (carcinogenic, mutagenic and repro-toxic) dangerous chemicals, dangerous CMR's) as well as the compounds contained in atmospheric pollution (dust, $SO_2$, NOx, CO, heavy metals, volatile organic compounds, fluorine, hydrochloric acid, etc., greenhouse gases such as $CO_2$, $CH_4$, $N_2O$, CFC's, HFC's, PFC's and $SF_6$ and other substances such as ozone, organochlorines (dioxins and furans), PAH's (Polycyclic Aromatic Hydrocarbons), etc.

The expression "microbiological agents" designates agents present in the air, food and drinking water, in particular bacteria, protozoans, viruses and fungi, and can be at the origin of various diseases.

According to a preferred embodiment, the hyaluronic acid defined above, comprises moreover a compound B chosen from vitamins, in particular ascorbic acid, vitamin E or tocopherol.

According to a preferred embodiment, the concentration of hyaluronic acid used above, is from 0.1 g/l to 4 g/l, and preferentially from 0.2 to 1 g/l. Below and above this concentration, the hyaluronic acid becomes inactive.

According to another preferred embodiment, the present invention relates to the use of at least one hyaluronic acid defined above for the preparation of a medicament intended for the treatment and/or prevention of pathologies caused by attacks originating from physical, chemical or microbiological agents.

According to a particularly preferred embodiment, the present invention relates to the use of a hyaluronic acid defined above, for the preparation of cosmetic and food compositions.

According to another embodiment, the hyaluronic acid defined above is used for the preparation of a medicament intended for the prevention of pathologies such as asthma, respiratory allergies, respiratory distress syndrome, in which the epithelial cells involved are cells of the mucous membranes of the upper and lower airways.

Asthma is a disease of the bronchial tubes which, during crises, leads to difficulties when breathing in and above all when breathing air out of the lungs. The crises can be triggered by different factors such as physical effort, humidity or dust or other allergens such as atmospheric pollutants.

Respiratory allergies are diseases triggered by allergens such as dust mites which are responsible for 70 to 80% of allergic asthma in children.

Among the other pneumallergens (allergens which penetrate the organism by respiratory route) in the indoor environment, domestic animals (cats, dogs, rodents), cockroaches and moulds, are a frequent source of respiratory allergy.

In the outdoor environment, atmospheric pollutants and atmospheric moulds can also be implicated.

Workplace allergens can also be responsible for sensitizations and respiratory allergies (most frequent sources: flour, laboratory animals, latex etc.).

Respiratory distress syndrome is a life-threatening respiratory distress due to an acute pulmonary impairment. It is caused by different factors such as the aspiration of hydrocarbons, the inhalation of irritant compounds (chlorine, $NO_2$, smoke, ozone, oxygen at high concentration, metal fumes, mustard gas), herbicides such as paraquat or opiates (such as heroin, morphine, dextropropoxyphene, or methadone).

Example 1 hereafter shows that the hyaluronic acid of the invention causes an increase in the functionality of the communicating junctions and therefore in this way makes it possible to prevent diseases in particular caused by atmospheric pollutants.

According to another embodiment, the hyaluronic acid defined above is used for the preparation of a composition intended for improving the protective function of the skin in the context of functional and structural disorders of the skin, in particular wrinkles, fine lines, a reduction in the tonicity and elasticity of the skin, dehydration of the skin, disorders in which the epithelial cells involved are skin cells.

The functional and structural disorders of the skin are the result of a slow, progressive, genetically programmed process and the attacks suffered by the skin daily, leading to aging of the latter.

A wrinkle is a linear furrow on the surface of the skin due to a fold of the epidermis and dermis.

Fine lines are furrows which are less pronounced than wrinkles and designate more particularly the wrinkles which form at the corner of the eye (crow's feet) and which are shallower than the other wrinkles that appear on the face.

The expression "tonicity of the skin" refers to slack, sagging skin.

The expression "elasticity of the skin" designates a skin which is stretched.

The expression "dehydration of the skin" designates a skin that does not retain enough water, causing it to lose its structure.

According to another embodiment, the hyaluronic acid defined above is used for the preparation of a composition intended for improving the protective function of the intestinal mucosa in the context of digestive disorders, in particular gastroenteritis, ischemic necroses and ulcerations of the intestinal mucosa, in which the epithelial cells involved are intestinal mucosa cells The digestive disorders encompass multiple symptoms which can affect all the organs of the digestive tract. The digestive disorders observed originate from a malfunction of these organs.

Gastroenteritis is an inflammatory infection characterized by the abrupt and frequent emission of liquid and copious feces.

Ischemic necrosis is a coagulation necrosis caused by a vascularization problem leading to the mummification of the cellular elements present.

Ulcerations of the intestinal mucosa lead to the destruction of the intestinal mucosa by invasion of the intestinal epithelium.

According to another embodiment, the hyaluronic acid defined above is used for the preparation of a composition intended for improving the protective function of the eye in the context of ocular disorders, in particular water stress, dryness of the eye, lesions of the cornea and keratitis, in which the epithelial cells involved are cells of the eye, and in particular of the cornea.

The expression "water stress" designates a lack of water in the eyeball.

If the tears are deficient in certain important components such as sebum or their production is insufficient, the tear film can degrade. Dry points then form on the cornea causing the symptoms of ocular dryness: itching, burning sensations, foreign bodies and general discomfort.

The expression "lesions of the cornea" designates a superficial defect of the epithelium of the cornea caused by abrasion or friction, usually due to a trauma or foreign body in the eye.

The term "keratitis" designates all the diseases involving the cornea, of traumatic, chemical, infectious or genetic origin. The diseases of the cornea are very numerous and result in a loss of transparency which can lead to a more or less complete and permanent loss of vision depending on the cause and the site of the lesions.

In another aspect, the present invention relates to the use of a combination of compounds having the following general formula (I):

$$(A,B) \qquad (I)$$

in which:
A is a hyaluronic acid as defined above,
B is chosen from the vitamins, in particular ascorbic acid and vitamin E or tocopherol, for the preparation of a medicament intended for the treatment and/or the prevention of pathologies caused by attacks originating from physical, chemical or microbiological agents, and in which the epithelial cells are involved, in particular the junction complexes of the latter.

The vitamins include the water-soluble vitamins such as vitamin B1 (thiamine), B2 (riboflavin), B3 (nicotinamide), B5 (pantothenic acid), B6 (pyridoxine), B8 (biotin), B9 (folic acid), B12 (cobalamin), C (ascorbic acid), PP (nicotinic acid) and the liposoluble vitamins such as vitamins A (retinol), D (calciferol), E (tocopherol), K1 (phylloquinone) and K2 (menaquinone).

Vitamin C and also vitamin E play the role of antioxidant in the context of formulae intended in particular for skin treatments.

In yet another aspect, the present invention relates to a pharmaceutical composition comprising at least one hyaluronic acid with a molecular weight from 30,000 to 45,000, preferentially 40,000 Daltons, or corresponding salts thereof at a concentration of 0.1 g/l to 1 g/l in combination with a pharmaceutically acceptable vehicle.

According to a preferred embodiment, the pharmaceutical composition defined above comprises moreover a compound B chosen from the vitamins, in particular ascorbic acid, vitamin E or tocopherol, in combination with a pharmaceutically acceptable vehicle.

According to another aspect, the present invention relates to a pharmaceutical composition comprising a compound of general formula (A, B) defined above, in combination with a pharmaceutically acceptable vehicle.

In a preferred embodiment, the pharmaceutical composition defined above is formulated to be administered by topical route at a dose comprised from 50 mg/d to 300 mg/d, preferentially from 100 mg/d to 200 mg/d or at a dose by oral route comprised from 0.66 mg/kg/d to 4 mg/kg/d, preferentially from 1.33 mg/kg/d to 2.66 mg/kg/d.

According to another embodiment, the pharmaceutical composition defined above is presented in enteric-coated form.

The expression "enteric-coated form" refers to a composition which is in the form of an enteric-coated vehicle, i.e. the hyaluronic acid is protected from the acidity of the stomach.

The physiologically stable enteric-coated vehicle is chosen from: enteric-coated microgranules, film-coated enteric-coated microgranules, enteric-coated nanoparticles, or nanospheres, enteric-coated microspheres, enteric-coated microcapsules, enteric-coated granules, film-coated enteric-coated granules, enteric-coated liposomes, film-coated enteric-coated liposomes, enteric-coated lyophilized tablets, film-coated enteric-coated lyophilized tablets, osmotic pumps with an enteric coating, gums, enteric-coated spheroids, enteric-coated spherules, film-coated enteric-coated spheroids, film-coated enteric-coated spherules, film-coated enteric-coated tablets, film-coated enteric-coated gelatin capsules.

According to another aspect, the present invention relates to a cosmetic composition comprising a hyaluronic acid with a molecular weight from 30,000 to 45,000, preferentially 40,000 Daltons, or corresponding salts thereof, at a concentration of 0.1 g/l to 1 g/l in combination with a cosmetically acceptable vehicle.

According to a preferred embodiment, the cosmetic composition defined above comprises moreover a compound of general formula B chosen from the vitamins, in particular ascorbic acid, vitamin E or tocopherol, in combination with a cosmetically acceptable vehicle.

According to yet another aspect, the present invention relates to a cosmetic composition comprising a compound of general formula (A, B) defined above, in combination with a cosmetically acceptable vehicle.

In a preferred embodiment, the cosmetic composition defined above is formulated to be administrable by topical route at a dose comprised from 1 mg/d to 300 mg/d, preferentially from 4 mg/d to 150 mg/d.

An example of a cosmetic composition is presented in Example 3 hereafter.

In another aspect, the present invention relates to a food composition comprising a hyaluronic acid with a molecular weight from 30,000 to 45,000, preferentially 40,000 Daltons, or corresponding salts thereof at a concentration of 0.1 g/l to 1 g/l.

According to a preferred embodiment, the food composition defined above comprises moreover a compound of general formula B chosen from the vitamins, in particular ascorbic acid, vitamin E or tocopherol.

In another aspect, the present invention relates to a food composition comprising a compound of general formula (A, B) defined above.

In a preferred embodiment, the food composition defined above is formulated to be administrable by oral route at a dose comprised from 50 mg/d to 300 mg/d, preferentially from 100 mg/d to 200 mg/d.

An example of a food composition is presented in Example 5.

In a preferred embodiment, the food composition defined above is presented in enteric-coated form.

An enteric-coated food composition can be presented in the form of tablets, gelatin capsules, sachets, or enteric-coated granules.

EXPERIMENTAL PART

Example 1

Example of the Increase on the Respiratory Epithelial Cells of the Expression of the Proteins Involved in Maintaining the Epithelial Integrity by the Use of Hyaluronic Acid Described in the Present Invention Respiratory epithelial cells are cultured in restriction rings containing DMEM/F12 medium supplemented with antibiotics, growth factors and with different concentrations of hyaluronic acid (0.1, 1.5 or 10 mg/ml) or in the absence of hyaluronic acid. At confluence, the restriction rings are removed in order to allow the migration of the cells on the periphery of the culture zone. The cells are then fixed then incubated successively with anti-ZO-1 or anti-Occludin antibodies, then with a biotinylated antibody and finally with steptavidin coupled to Alexa Fluorine 488 (Invitrogen). The preparations are mounted on a glass slide in a solution which makes it possible to prevent photobleaching and observed using a fluorescence microscope at a magnification of ×40 in order to visualize the cellular localization of the ZO-1 proteins and occludin.

In another series of experiments, two different extractions were carried out on cell cultures: an extraction of total proteins and an extraction of membrane proteins in order to evaluate the expression of ZO-1 and occludin by the Western Blot technique.

The functionality of the tight junctions was evaluated by measurement of the transepithelial resistance: the respiratory epithelial cells are cultured in a culture dish with a double compartment making it possible to measurement the epithelial resistance. This measurement is carried out every 24 hours using a double electrode which allows a constant tension to be established between the apical medium and the basal medium of the culture chamber. Measurement of the induced current makes it possible to calculate the resistance of the layer of cells. The increase in the trans-epithelial resistance results in the presence of functional tight junctions.

The functionality of the communicating junctions was evaluated using video-microscopy and FRAP (fluorescence recovery after photobleaching) techniques: measurement of the diffusion of a fluorescent probe via the communicating junctions. (Abaci M et al., Biotechnol J, 2007.2: 50-61; Tedelind S, Eur J Endocrinol 2003, 149:215-221)

Results:

Effect of Hyaluronic Acid on the Expression of the Defence Proteins

Expression of ZO-1 and Occludin Evaluated by Immunocytochemistry

Figure 1:
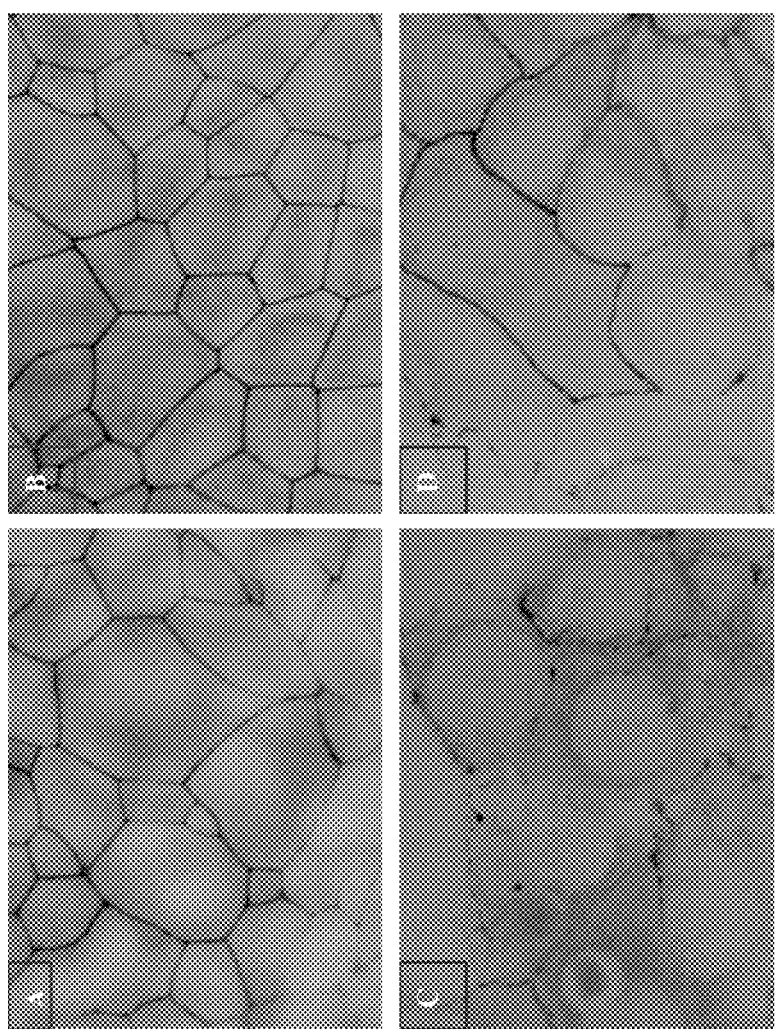
FIG. 1 represents the immunolocalization of the junction protein ZO-1. In the zones of confluent cells, the localization of ZO-1 does not differ depending on whether the cells have been incubated or not incubated with hyaluronic acid, but the network formed by ZO-1 is denser when the cells have been incubated with hyaluronic acid (A,B). On the other hand, at the level of the cells situated on the periphery of the culture and which are dedifferenciated, it is observed that the expression of ZO-1 is more significant and more continuous when the cells are incubated with hyaluronic acid (D), compared to the cells which have not been incubated with hyaluronic acid (C). The same expression profile is observed for the junction protein occludin.

In the zones of confluent cells, the localization of ZO-1 does not differ depending on whether the cells have been incubated or not with the hyaluronic acid. On the other hand, at the level of the cells situated on the periphery of the culture and which are dedifferenciated, it is observed that the expression of ZO-1 is more significant and more continuous when the cells are incubated with hyaluronic acid, compared to cells which have not been incubated with hyaluronic acid (FIG. 1).

The same expression profile is observed for the junction protein occludin.

Expression of ZO-1 and Occludin Evaluated by Western Blot

Figure 2:
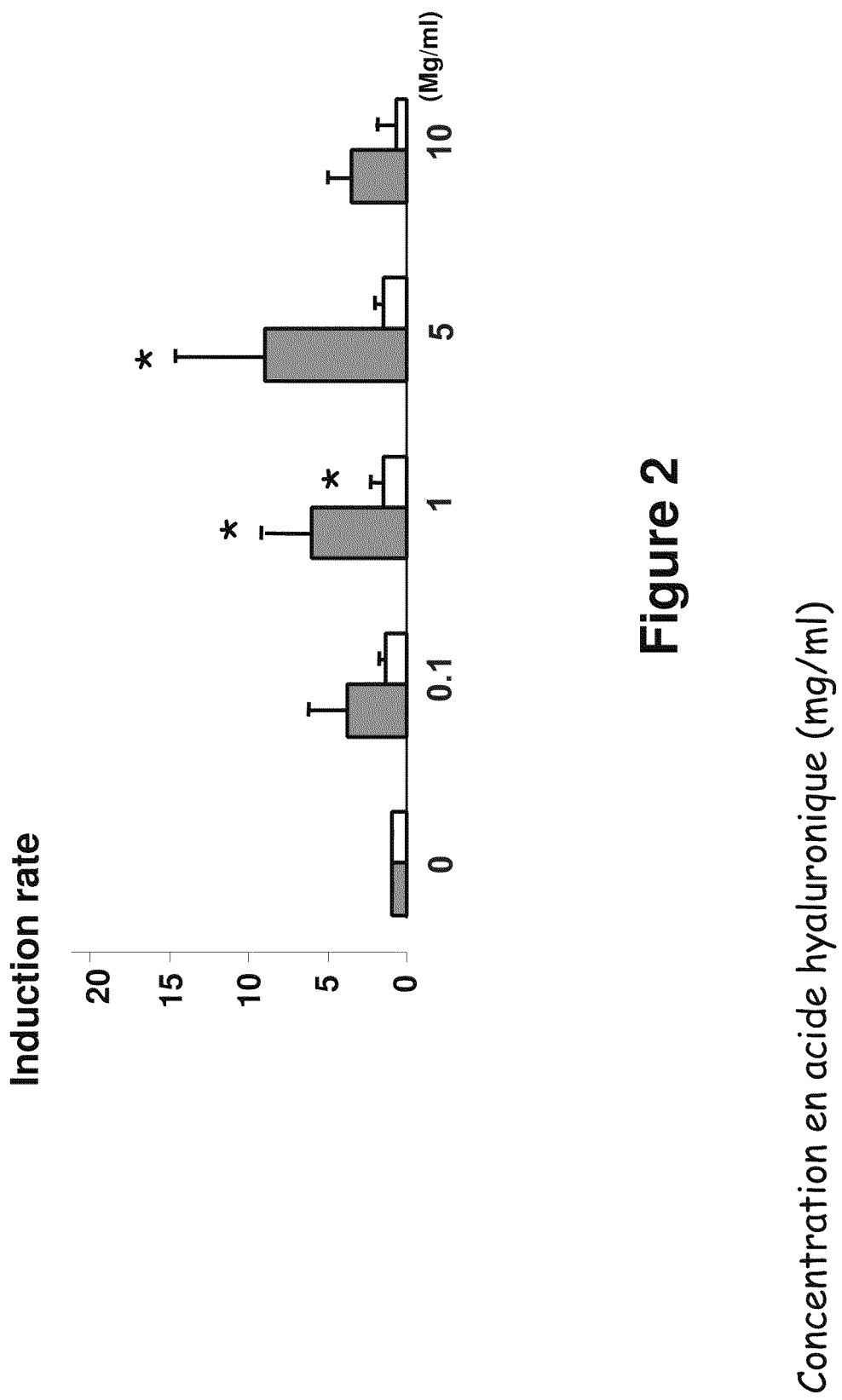
FIG. 2 represents the effect of the concentration of hyaluronic acid (x-axis) on the membrane expression of the ZO-1 proteins and occludin (y-axis). The columns in white correspond to occludin and the columns in grey to ZO-1. The stars indicate a significant statistical difference ($p<0.05$) with respect to the control without hyaluronic acid.

The rates of expression at the level of the membrane of the junction proteins ZO1 and occludin in the presence of increasing concentrations of hyaluronic acid are represented in FIG. 2. The quantity of protein measured in the presence of hyaluronic acid is expressed as a function of the quantity of protein measured in the absence of hyaluronic acid. The values represented to the average± the standard error of 4 experiments.

A significant increase ($p<0.05$) in the expression of the protein ZO1 is observed when the cells are incubated in the presence of hyaluronic acid at a concentration of 1 and 5 mg/ml. A significant increase ($p<0.05$) in the expression of occludin is also noted when the cells are incubated in the presence of hyaluronic acid at a concentration of 1 mg/ml.

Analysis of the Functionality of the Communicating Junctions

Figure 3:
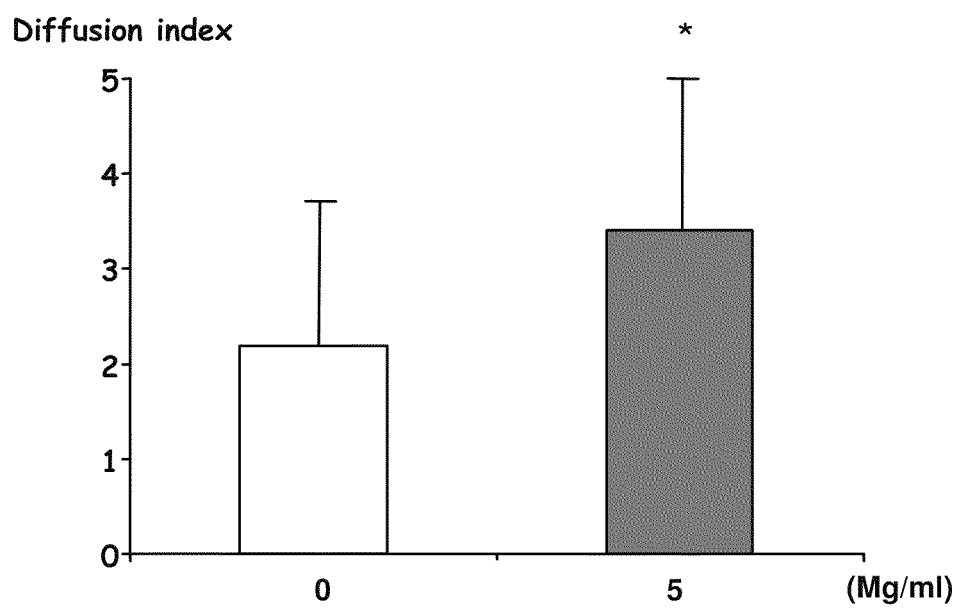
FIG. 3 represents the effect of hyaluronic acid (x-axis) on the functionality of the communicating junctions (y-axis). The column in white corresponds to the control without hyaluronic acid and the column in grey corresponds to hyaluronic acid at 5 mg/ml. The star indicates a significant statistical difference ($p<0.05$) with respect to the control.

The functionality of the communicating junctions was evaluated by measurement of the intercellular diffusion of a fluorescent molecule. FIG. 3 shows that the incubation of respiratory epithelial cells in the presence of hyaluronic acid (5 mg/ml) induces a significant increase ($p<0.05$) in the diffusion index, which results in an increase in the functionality of the communicating junctions.

Example 2

Example of the Increase on Skin Cells of the Expression of the Proteins Involved in Maintain Cell Contiguity by the Use of Hyaluronic Acid Described in the Present Invention Normal human keratinocytes originating from the explant from plastic surgery (Normal Human Epidermal Keratinocytes; NHEK's) are incubated in an SFM medium (Invitrogen 17005075) complemented with growth factors such as EGF (Epidermal Growth Factor) 0.25 ng/ml, hypophysis extract 25 µg/ml (Invitrogen 37000015), gentamicin 25 µg/ml (Sigma G1397), for 24 hours at 37° C. and under 5% $CO_2$ then the medium is eliminated and the cells are placed in the presence or not (control) of the hyaluronic acid molecule of the invention. The hyaluronic acid concentrations tested are 0.1 mg/ml, 1 mg/ml and 5 mg/ml.

After incubation for 72 hours at 37° C. and 5% $CO_2$, the culture medium is eliminated then the cells are rinsed with a phosphate buffer then immediately frozen at −80° C.

The total proteins expressed by the cells are extracted then placed in contact with an anti-ZO1 antibody (Cliniscience 33-9100) and an anti-occludin antibody (Cliniscience 33-1500) coupled to a detection system involving a second antibody conjugated with a peroxidase. The expression of the colouration in the presence of the peroxidase substrate provides information on the expression of the ZO1 and occuldin markers as a function of the quantity of HA present in the medium.

Figure 4:
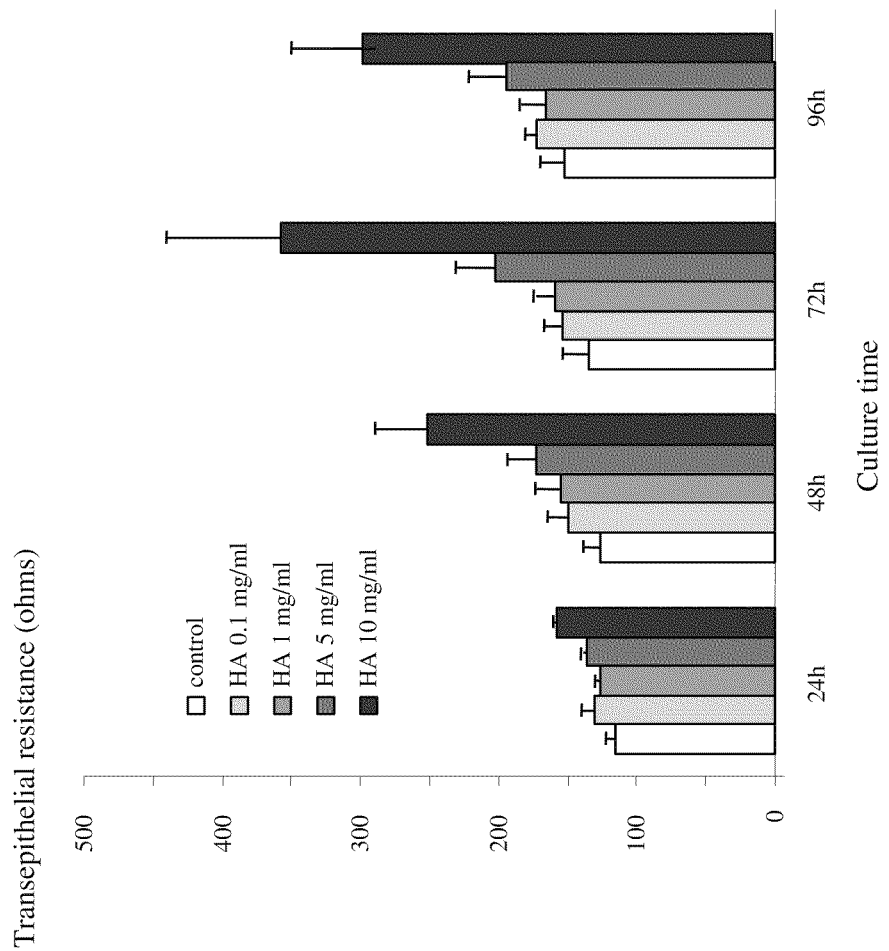
FIG. 4 represents the effect of the concentration of hyaluronic acid and culture time of the respiratory epithelial cells (x-axis) on the transepithelial resistance (y-axis). A significant increase ($p<0.02$) in the transepithelial resistance is observed as a function of time and hyaluronic acid concentration.
Figure 5:
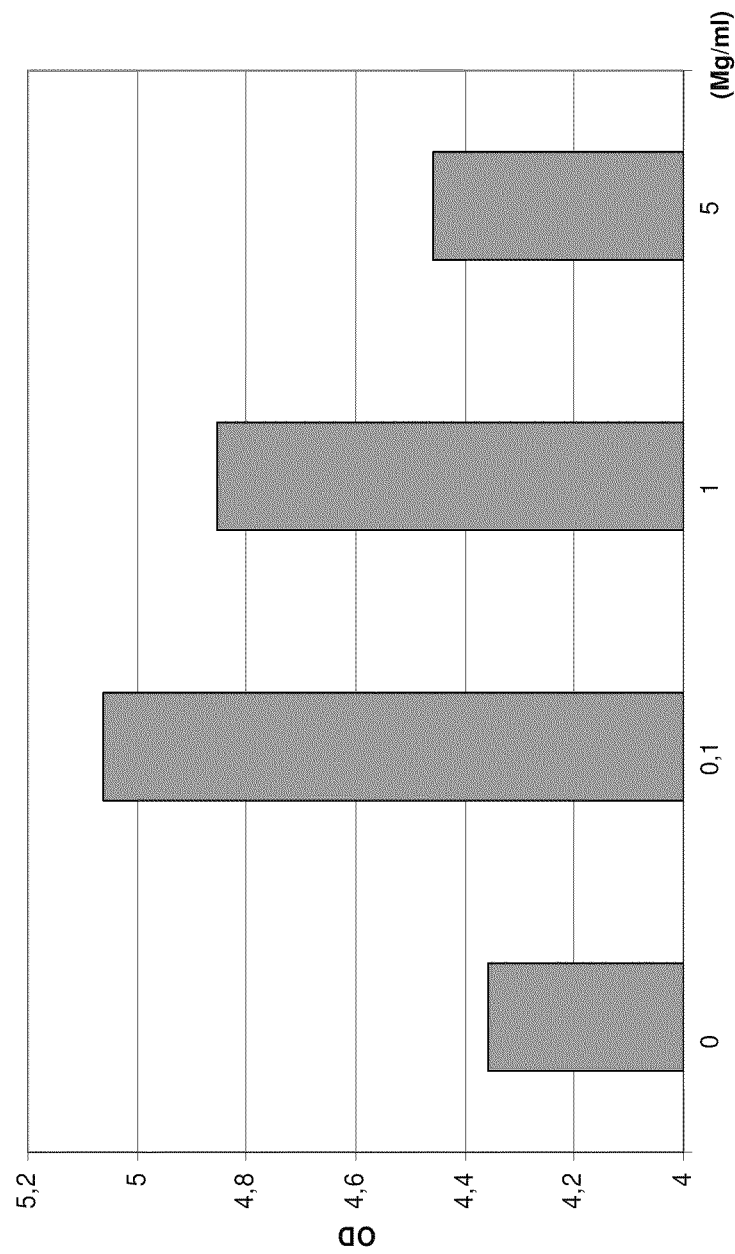
FIG. 5 represents the effect of the concentration of hyaluronic acid (x-axis) on the expression of the occludin proteins of skin cells (y-axis). The diagrams correspond to measurements of the intensity of expression of the peroxidase activity. The values are the averages of three points.

In FIGS. 4 and 5 an increase in the expression of the junction proteins occludin and ZO-1 is observed when the cells are incubated with hyaluronic acid of the invention. It should be noted that the maximum expression is obtained at a concentration of 0.1 mg/ml for occludin and 1 mg/ml for ZO-1 protein.

The skin, which is one of the organs most exposed to multiple attacks by the environment, may be better able to resist various attacks such as atmospheric pollution when the latter is in contact with an HA of low molecular weight making it possible to increase the cohesion between the cells.

Example 3

A cosmetic composition intended for the skin containing the molecule of the invention is represented by the following formula:

| | |
|---|---|
| Emulsifier | 4% |
| Preservative | 0.5% |
| Glycerol | 5% |
| Polymer of the invention | 0.01% to 0.1% |
| NaCl | 0.5% |
| Water | QS 100 |

Example 4

Example of the Increase on of the Intestinal Cells of the Expression of the Proteins Involved in Maintaining Cell Contiguity by the Use of the Hyaluronic Acid Described in the Present Invention Human colon cells (Epithelial Human Caucasian Colon adenocarcinoma R51, Caco-2) are incubated in an MEM medium (Invitrogen 21090-022) complemented with nonessential amino acids (Invitrogen 11140-035), Glutamine 2 mM (Invitrogen 25030024), penicillin 50 IU/ml, streptomycin 50 µg/ml (Invitrogen 15070063) 10% foetal calf serum (FCS, Invitrogen 10270098) for 24 hours at 37° C. and under 5% $CO_2$ then the medium is eliminated and the cells are placed in the presence or not (control) of the hyaluronic acid molecule of the invention. The concentrations of hyaluronic acid tested are 0.1 mg/ml, 1 mg/ml and 5 mg/ml.

After incubation for 72 hours at 37° C. and 5% $CO_2$, the culture medium is eliminated then the cells are rinsed with a phosphate buffer then immediately frozen at −80° C.

The total proteins expressed by the cells are extracted then placed in contact with an anti-ZO1 antibody (Cliniscience 33-9100) and anti-occludin antibody (Cliniscience 33-1500) coupled to a detection system involving a second antibody conjugated with a peroxidase. The expression of the colouration in the presence of the peroxidase substrate provides information on the expression of the ZO1 and occludin markers as a function of the quantity of HA present in the medium.

Figure 6:
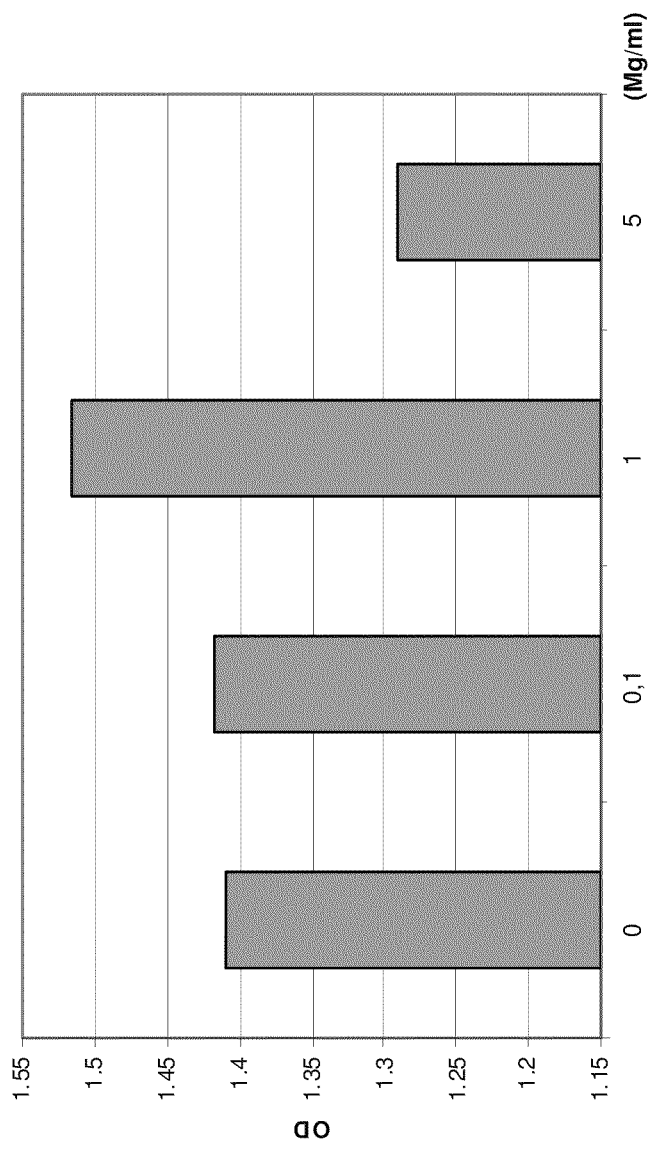
FIG. 6 represents the effect of the concentration of hyaluronic acid (x-axis) on the expression of the ZO-1 proteins of skin cells (y-axis). The diagrams correspond to measurements of the intensity of expression of the peroxidase activity. The values are the averages of three points.
Figure 7:
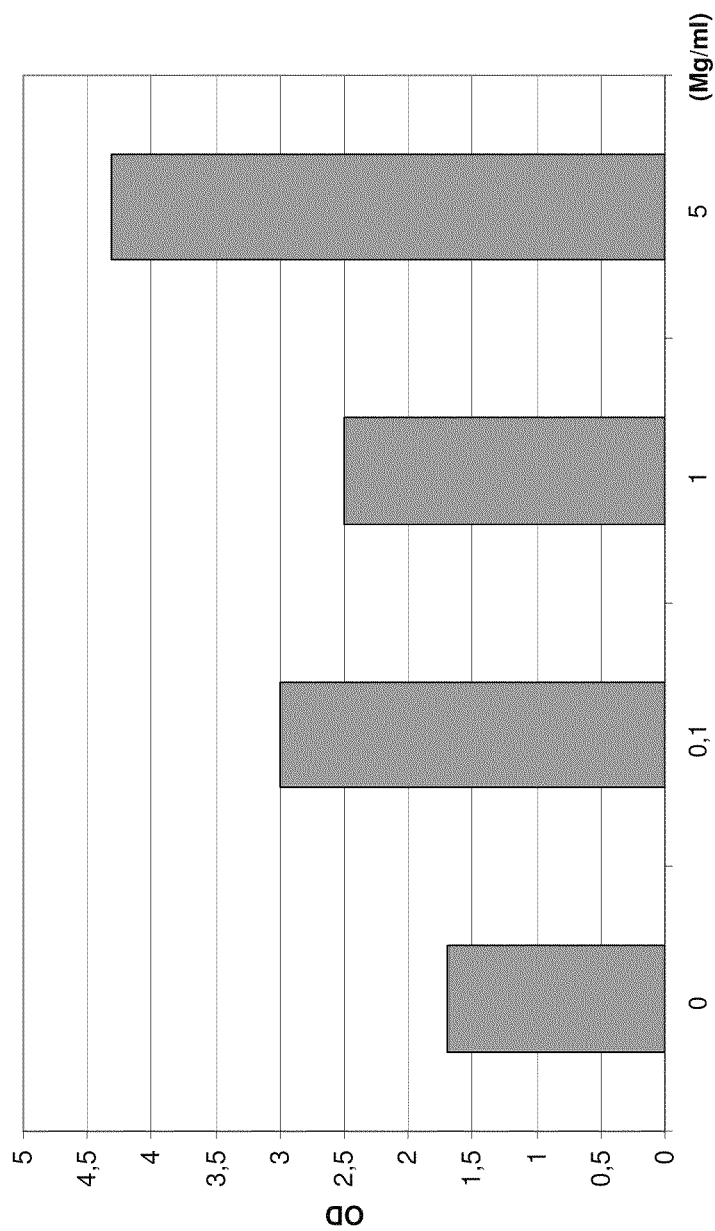
FIG. 7 represents the effect of the concentration of hyaluronic acid (x-axis) on the expression of the occludin proteins of intestinal cells (y-axis). The diagrams hereafter correspond to measurements of the intensity of the expression of the peroxidase activity. The values are the averages of three points.
Figure 8:
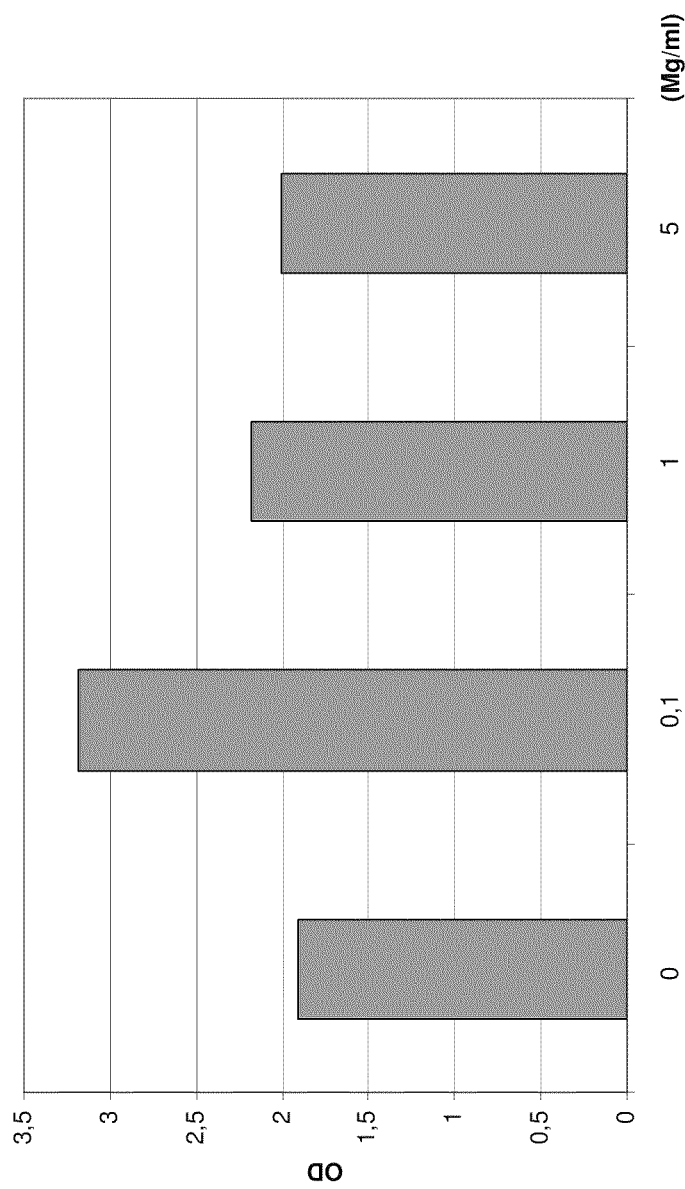
FIG. 8 represents the effect of the concentration of hyaluronic acid (x-axis) on the expression of the ZO-1 proteins of intestinal cells. The diagrams hereafter correspond to measurements of the intensity of the expression of the peroxidase activity. The values are the averages of three points.

In FIGS. 6 and 7 it appears that the expression of the junction proteins occludin and ZO1 is modulated by the presence of the hyaluronic acid of the invention.

The occludin is expressed in greater quantity at a high concentration of hyaluronic acid whereas, as regards the ZO1 protein, the maximum expression is observed at a concentration of 0.1 mg/ml.

Contact between the cells of the digestive tract by ingestion of hyaluronic acid of low molecular weight for example, allows an increase in the expression of the junction proteins which results in a reinforcement of the defence functions performed by the epithelial barrier.

Example 5

A food composition intended for the intestinal mucosa containing the molecule of the invention is represented by the following formula:

| Polymer of the invention | 0.01% to 0.1% |
|---|---|
| Magnesium stearate | 0.1% |
| Excipient: rice starch | QS 1 gram |
| Capsule | Gelatin |

The invention claimed is:

1. A method for treating the mucous membranes of the eye in the context of ocular disorders, comprising administering to a person in need thereof of at least one hyaluronic acid with a molecular weight from 30,000 to 45,000 Daltons or corresponding salts thereof,
wherein the at least one hyaluronic acid is administered at a concentration from 0.1 g/l to 4 g/l,
and
wherein the ocular disorders are select from group consisting of dryness of the eye, lesions of the cornea, and keratitis.

2. The method according to claim 1, further comprising the administration of a compound B chosen from the vitamins.

3. The method according to claim 1, wherein the method treats ocular disorders caused by attacks originating from physical, chemical or microbiological agents.

4. The method according to claim 1, wherein hyaluronic acid has a molecular weight of 40,000 Daltons.

5. The method according to claim 1, wherein hyaluronic acid is administered at a concentration from 0.2 to 1 g/l.

6. The method according to claim 2, wherein the vitamins are selected from the group consisting of ascorbic acid, vitamin E or tocopherol.

7. The method according to claim 4, further comprising the administration of a compound B chosen from the vitamins.

8. The method according to claim 4, wherein hyaluronic acid is administered at a concentration from 0.2 to 1 g/l.

9. The method according to claim 4, wherein the method treats ocular disorders caused by attacks originating from physical, chemical or microbiological agents.

10. A method for treating the mucous membranes of the eye in the context of disorders of the eye, comprising administering to a person in need thereof of at least one hyaluronic acid with a molecular weight of 30,000, 40,000 or 45,000 Daltons or corresponding salts thereof,
wherein the at least one hyaluronic acid is administered at a concentration from 0.1 g/l to 4 g/l,
and
wherein the disorders of the eye are selected from the group consisting of dryness of the eye, lesions of the cornea, and keratitis.

11. The method according to claim 10, further comprising the administration of a compound B chosen from the vitamins.

12. The method according to claim 10, wherein the method treats disorders caused by attacks originating from physical, chemical or microbiological agents.

13. The method according to claim 10, wherein hyaluronic acid has a molecular weight of 40,000 Daltons.

14. The method according to claim 10, wherein hyaluronic acid is administered at a concentration from 0.2 to 1 g/l.

15. The method according to claim 11, wherein the vitamins are selected from the group consisting of ascorbic acid, vitamin E or tocopherol.

16. The method according to claim 13, further comprising the administration of a compound B chosen from the vitamins.

17. The method according to claim 13, wherein hyaluronic acid is administered at a concentration from 0.2 to 1 g/l.

18. The method according to claim 13, wherein the method treats disorders caused by attacks originating from physical, chemical or microbiological agents.

* * * * *